(12) United States Patent
Walsdorff et al.

(10) Patent No.: US 8,003,837 B2
(45) Date of Patent: Aug. 23, 2011

(54) CATALYSTS FOR DEHYDROGENATION AND/OR HYDROGENATION OF HYDROCARBONS, PROCESSES FOR PREPARING THE SAME, AND USES THEREFOR

(75) Inventors: Christian Walsdorff, Ludwigshafen (DE); Christophe Houssin, Mannheim (DE); Gerald Vorberg, Speyer (DE); Reinhard Koerner, Frankenthal (DE); Otto Hofstadt, Speyer (DE)

(73) Assignee: BASF SE (DE)

( * ) Notice: Subject to any disclaimer, the term of this patent is extended or adjusted under 35 U.S.C. 154(b) by 651 days.

(21) Appl. No.: 11/996,372

(22) PCT Filed: Jul. 13, 2006

(86) PCT No.: PCT/EP2006/064178
§ 371 (c)(1),
(2), (4) Date: Jan. 22, 2008

(87) PCT Pub. No.: WO2007/009927
PCT Pub. Date: Jan. 25, 2007

(65) Prior Publication Data
US 2008/0200739 A1    Aug. 21, 2008

(30) Foreign Application Priority Data

Jul. 22, 2005  (DE) .......................... 10 2005 034 978

(51) Int. Cl.
*C07C 5/00* (2006.01)
*C07C 5/327* (2006.01)
*B01J 23/00* (2006.01)

(52) U.S. Cl. ......... 585/250; 585/654; 502/336; 502/338
(58) Field of Classification Search .................. 502/336, 502/338; 585/250, 654
See application file for complete search history.

(56) References Cited

U.S. PATENT DOCUMENTS

| | | | | |
|---|---|---|---|---|
| 4,888,316 A | * | 12/1989 | Gardner et al. ................. | 502/20 |
| 5,242,483 A | * | 9/1993 | Ramirez de Agudelo et al. .............................. | 75/507 |
| 5,559,066 A | * | 9/1996 | Poepel et al. ................... | 502/20 |
| 7,186,395 B2 | | 3/2007 | Walsdorff et al. | |
| 2003/0144566 A1 | | 7/2003 | Culp et al. | |

FOREIGN PATENT DOCUMENTS
CA            2558547 A1      10/2005
(Continued)

*Primary Examiner* — Cam N Nguyen
(74) *Attorney, Agent, or Firm* — Connolly Bove Lodge & Hutz LLP

(57) ABSTRACT

Catalysts comprising: a ground, spent (de)hydrogenation catalyst material present in an amount of 10 to 70% by weight based on the catalyst, the ground, spent catalyst material comprising iron oxide; and a fresh catalyst material present in an amount of 30 to 90% by weight based on the catalyst, the fresh catalyst material comprising iron oxide, wherein at least a portion of the iron oxide in the fresh catalyst material comprises a phase selected from the group consisting of hematite, potassium ferrite, and mixtures thereof are described along with processes for preparing and using the same.

12 Claims, 1 Drawing Sheet

FOREIGN PATENT DOCUMENTS

Figure 1:
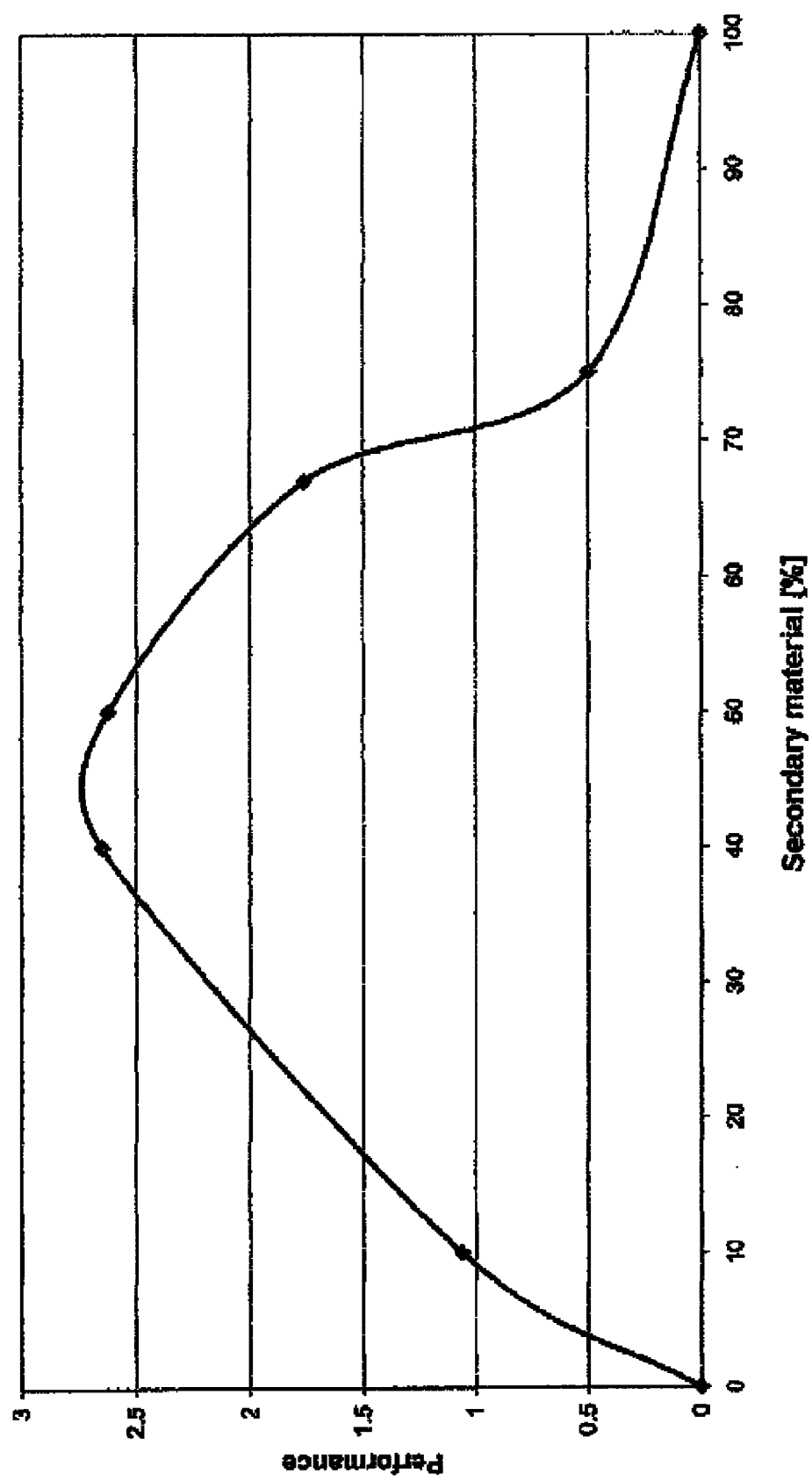

| | | |
|---|---|---|
| DE | 130793 | 5/1978 |
| DE | 268631 A1 | 6/1989 |
| DE | 4006918 A1 | 9/1991 |
| DE | 10154718 A1 | 5/2003 |
| DE | 10305650 A1 | 8/2004 |
| EP | 02/083569 A2 | 10/2002 |
| EP | 1379470 | 1/2004 |
| GB | 626742 | 7/1949 |
| WO | WO-94/11104 A1 | 5/1994 |
| WO | WO-2005/097715 A1 | 10/2005 |
| WO | WO-2006/018133 A1 | 2/2006 |
| WO | WO-2006/067169 A1 | 6/2006 |

* cited by examiner

CATALYSTS FOR DEHYDROGENATION AND/OR HYDROGENATION OF HYDROCARBONS, PROCESSES FOR PREPARING THE SAME, AND USES THEREFOR

CROSS-REFERENCE TO RELATED APPLICATIONS

This application is a national stage application, under 35 U.S.C. §371, of PCT/EP2006/064178, filed Jul. 13, 2006, which claims priority of German Patent Application No. 10 2005 034 978.1, filed Jul. 22, 2005.

BACKGROUND OF THE INVENTION

The regeneration of secondary catalyst material has been of particular interest in the chemical industry for many years, since the reuse involves a resource and cost saving.

The field of dehydrogenation catalysts includes the following prior art:

DD 268 631 A1 describes dehydrogenation catalysts which consist of from 50 to 90 parts of waste iron oxides with the composition of from 10 to 40% magnetite, from 50 to 80% goethite and from 10 to 30% lepidocrocite (waste 1), from 1 to 20 parts of waste iron oxides with the composition of from 85 to 95% magnetite (waste 2) and from 5 to 15% wuestite and from 49 to 10 parts of ground spent styrene catalyst. No thermal treatment of the ground spent catalysts is described; it is merely mixed with the other wastes before the further processing. Waste 1 and 2 arises, for example, in the production of pigments for data carriers owing to the high qualitative requirements with regard to the magnetic properties. The dehydrogenation catalyst described achieves a conversion of approx. 40% with a selectivity of approx. 92% in the dehydrogenation of ethylbenzene to styrene.

WO 94/11104 discloses a process for preparing dehydrogenation catalysts comprising iron, potassium and cerium from such spent catalysts by grinding the spent material, if appropriate purifying, restoring the original action by adjusting the composition and restoring the external shape by adding to the ground spent material an effective amount of potassium and such an amount of cerium that the total amount of cerium is higher than the amount originally present. If appropriate, the spent material is calcined in the presence of oxygen before grinding. The process described affords dehydrogenation catalysts which achieve a selectivity of from 94 to 95% with a conversion of 70% in the dehydrogenation of ethylbenzene to styrene.

In other catalytic processes too, for example in the removal of nitrogen oxides from combustion gases by reaction with ammonia at elevated temperature, a regeneration of the spent catalyst material is described (DE 40 06 918 A1), by grinding the spent catalysts to particle sizes of from 5 to 20 μm and adding the resulting powder in the preparation of catalysts with fresh starting material in amounts of up to 80% by weight based on the overall material used before the shaping.

DE 103 05 650 A1 describes the regeneration of mixed oxide catalysts which are used in the ammoxidation to prepare nitriles. The deactivated catalyst is ground if appropriate and calcined under oxygen at from 300 to 900° C.

The prior art describes various catalysts and processes for dehydrogenating and hydrogenating hydrocarbons. The (de)hydrogenation catalysts described are typically supplied in the form of strands, rings, tablets, annular tablets, extrudates, honeycombs or similar moldings. The active composition of the catalysts mentioned comprises predominantly metals selected from the group consisting of iron, alkali compounds, especially potassium, molybdenum, magnesium, calcium, cerium, tungsten, titanium, vanadium, copper, manganese, nickel, zinc, palladium, platinum, cobalt aluminum, tin, silicon, lead, ruthenium, silver, gold, zirconium, rhodium, lanthanum, chromium, cadmium or barium.

The (de)hydrogenation catalysts are prepared in relatively recent prior art and on the industrial scale, however, still by the following processes (see, inter alia, EP-A 1 379 470):

a) The fresh feedstocks in the form of metal oxides, nitrates, carbonates, hydroxides or the like are mixed directly in a mixer, kneader or Mix-Muller. The feedstocks may also be slurried in a spray slurry and processed to a spray powder in a spray dryer. The extrudable mass is subsequently extruded, dried and calcined.

b) The fresh feedstocks are obtained via precipitation reactions, processed to a spray powder in a spray dryer, calcined and reshaped, or first reshaped and then calcined.

When a catalyst, after a running time of typically from two to five years of operation in an industrial plant, for example an isoprene, butadiene or styrene plant, is deinstalled, the catalyst has experienced a number of changes. The deinstalled catalyst generally has iron oxide in a reduced form, i.e. as magnetite. Some of the deinstalled catalyst has generally been depleted of potassium compounds, while an enrichment of potassium compounds may also be present in the form of separate deposits between the catalyst strands in other regions, especially in the interior of the catalyst molding. The potassium is typically present in the form of potassium carbonate or potassium hydrogencarbonate. The deinstalled catalysts generally have virtually no organic hydrocarbons or coke deposits whatsoever, i.e. carbon which is not present as carbonate or hydrogencarbonate. The cerium crystal size of the deinstalled catalysts is from about 40 to 60 nm.

The catalyst moldings have often been damaged by the mechanical stresses in the course of installation, operation and deinstallation. Moreover, the deinstalled catalysts may comprise a high fraction of dust or fragments.

Owing to the changes detailed in the secondary catalyst material and the general difficulties in the processing of secondary catalyst material, especially in the course of extrusion, predominantly catalysts which have been prepared from fresh feedstocks have been used to date in industrial (de)hydrogenation processes.

In view of high raw material prices and rising demands on the sustainability of economic activity, processes for using secondary raw materials are increasingly in the focus of chemical research. Moreover, increasingly higher demands are being made on the disposal of spent catalysts from the chemical industry.

BRIEF SUMMARY OF THE INVENTION

The invention relates to a catalyst for dehydrogenating or hydrogenating hydrocarbons comprising from 10 to 70% by weight of ground secondary catalyst material of spent (de)hydrogenation catalyst comprising iron oxide and from 30 to 90% by weight of the corresponding fresh catalyst material comprising iron oxide, the iron oxide of the fresh catalyst material being present predominantly in the form of hematite or potassium ferrite phases. The invention further relates to a process for preparing the inventive catalyst. The invention further relates to a process for dehydrogenating or hydrogenating hydrocarbons using the inventive catalyst.

It was therefore an object of the present invention to discover a process in order to prepare catalysts for significant processes in the chemical industry using secondary catalyst material as a feedstock. In particular, it is an object of the present invention to prepare catalysts comprising iron oxides using secondary catalyst material. The catalyst prepared using secondary catalyst material should have comparable properties, especially with regard to activity, selectivity and, in particular, mechanical hardness, to the catalysts from the prior art. Moreover, the secondary catalyst material should be usable directly without adding doping elements.

The invention accordingly relates to catalysts for dehydrogenating or hydrogenating hydrocarbons comprising from 10 to 70% by weight of ground secondary catalyst material of a spent (de)hydrogenation catalyst comprising iron oxide and from 30 to 90% by weight of the corresponding fresh catalyst material comprising iron oxide, the iron oxide of the fresh catalyst material being present predominantly in the form of hematite or potassium ferrite phases.

In the present invention, the term "secondary catalyst material" is understood to mean catalyst material already spent/used/deactivated and, if appropriate, reprocessed. The secondary catalyst material has thus already been installed once into a chemical plant, the chemical plant has been operated for a period of from several days to several years and the catalyst material has been deinstalled again. In particular, the secondary catalyst material has been used for a typical lifetime of (de)hydrogenation catalysts of from 1 to 3 years.

DETAILED DESCRIPTION OF THE INVENTION

The secondary catalyst material advantageously does not have any organic hydrocarbons or coke deposits. Overall, such deposits should advantageously make up less than 2% by weight, preferably less than 1% by weight, especially less than 0.1% by weight, based on the secondary catalyst material.

A small amount of deposits can be achieved by a specific shutdown, known to those skilled in the art, of the isoprene, butadiene or styrene plant.

Advantageously, in the course of shutdown of a plant, the temperature is reduced to from 580 to 610° C. Subsequently, the ethylbenzene feed is reduced so as to give rise to a steam/ethylbenzene weight ratio of at least 2/1. After the vacuum has been shut down, the temperature is lowered further to from 550 to 575° C. and, simultaneously, the ethylbenzene feed is reduced in stages and finally shut down. Subsequently, the nitrogen circulation is switched on and the temperature is lowered further down to a minimum of 360° C., preferably 400° C. Once the steam circulation has been shut down, the temperature is lowered to 50° C. under nitrogen. At at least 30° C., preferably at approx. 50° C., air is added in a controlled manner. The control is effected with the aid of thermoelements which detect local temperature increases, i.e. reoxidation. When no temperature increases are discernable any longer, further air can be added until no further temperature increases are discernable. Finally, cooling is effected with air and nitrogen or only with air.

Advantageously, the deinstalled secondary catalyst material, before reuse, is subjected to a thermal treatment under an oxygenous atmosphere. The thermal treatment is carried out advantageously at temperatures of from 100 to 1500° C., preferably from 300 to 1200° C., more preferably from 500 to 1000° C. even more preferably from 700 to 1000° C. and in particular from 850 to 1000° C. Appropriately, the thermal treatment is carried out for a period of from 30 minutes to 10 hours, preferably for a period of from 1 to 3 hours.

After the thermal treatment, the iron is advantageously present essentially in the form of hematite, magnetite and potassium ferrite phases. Accordingly, the secondary catalyst material advantageously has iron predominantly in the form of $K_2Fe_xO_y$, hematite and magnetite, where x is advantageously between 1 and 11 and y is advantageously between 2 and 17. Preferred potassium ferrite phases are $K_2Fe_{10}O_{16}$ and $KFeO_2$. The iron oxide is present advantageously at from 15 to 85% by weight, based on the sum of the iron oxides, in the form of $K_2Fe_xO_y$, advantageously at from 20 to 60% by weight. The remaining iron oxides are advantageously present in the form of hematite and/or magnetite.

After the thermal treatment, the secondary catalyst material advantageously has a cerium crystal size of from 15 to 90 nm, preferably from 40 to 60 nm.

The oxygenous gas used is preferably air. Depending on the source from which the air originates, its composition may vary within the limits familiar to those skilled in the art. Particular preference is given to using lean air.

The thermal treatment may be carried out batchwise or continuously in various apparatus, for example in tray ovens or rotary tubes. Preference is given to carrying out the thermal treatment continuously in rotary tubes. Especially in the case of highly pulverized or pulverulent deinstalled catalyst, it may be advisable to perform the calcination in a rotary tube equipped with tappers. Moreover, the oxidative treatment can also be performed before the deinstallation of the secondary catalyst material directly in the production plant.

The secondary catalyst material is advantageously, if appropriate after a thermal treatment, ground in suitable mills. In some cases, it may be advantageous to initially precrush the material. This precrushing can be effected, for example, in cam crushers or hammer mills with, for example, a 3 mm square-hole screen at, for example, 3000 revolutions per minute. Subsequently, the material can, for example, be finally comminuted with a spiral jet mill. The grinding gas pressure in the course of grinding is typically from 1 to 10 bar. The grinding throughput is generally from 1 to 30 kg/h.

The mean particle diameters have a value in the range from 1 to 700 µm, preferably from 5 to 500 µm, in particular from 10 to 200 µm.

The ground secondary catalyst powder can subsequently be used for the preparation of new catalysts.

The inventive catalyst comprises advantageously from 15 to 70% by weight of ground secondary catalyst material, based on the overall catalyst material, and from 30 to 85% by weight of the corresponding fresh catalyst material, based on the overall catalyst material, preferably from 25 to 65% by weight of ground secondary catalyst material and from 35 to 75% by weight of the corresponding fresh catalyst material, especially from 35 to 55% by weight of ground secondary catalyst material and from 45 to 65% by weight of the corresponding fresh catalyst material.

The inventive catalyst advantageously comprises exclusively secondary and fresh catalyst material in the ratios specified.

The bulk density of the inventive catalyst is advantageously from 1.2 to 2 kg/l, especially from 1.3 to 1.7 kg/l. The tapped density is advantageously from 1 to 1.7 kg/l, especially from 1.1 to 1.5 kg/l.

If appropriate, an elemental analysis is performed on the ground secondary catalyst powder. Normally, the catalytic composition of the fresh feedstocks corresponds to the catalytic composition known from the prior art for (de)hydrogenation catalysts. In exceptional cases, owing to the analyzed composition of the ground secondary catalyst powder, the amount and the typical composition of the fresh feedstocks can be altered.

The inventive catalysts advantageously comprise feedstocks in the form of oxides, nitrates, carbonates, hydroxides and the like, preferably in the form of oxides, especially iron, preferably as iron oxide, appropriately in an amount of from 40 to 90% by weight based on the sum of all feedstocks. In addition, the inventive catalysts advantageously comprise alkali metal compound(s), preferably potassium compound(s), for example potassium oxide, appropriately in an amount of from 1 to 40% by weight based on the sum of all feedstocks. Typically, the inventive catalysts advantageously comprise a series of promoters depending on their field of use.

The inventive catalyst is suitable especially for dehydrogenating hydrocarbons which have at least one saturated functional group, for example alkenes to the corresponding 1,3-alkadienes, preferably alkylaromatic compounds to the corresponding alkenylaromatic compounds. Suitable alkylaromatic compounds are all aromatic and heteroaromatic alkyl compounds; preference is given to those in which the alkyl radical is unbranched or branched and comprises from two to six carbon atoms. Suitable aromatic radicals are mono-, bi- or tricyclic, preferably mono- or bicyclic, more preferably monocyclic aromatics. Examples include isopropylbenzene (cumene), ethylbenzene, 1,1-diphenylbenzene and 1,2-diphenylethane (bibenzyl), preferably isopropylbenzene (cumene), ethylbenzene and 1,1-diphenylbenzene, more preferably ethylbenzene. Suitable heteroaromatic radicals are mono-, bi- or tricyclic, preferably mono- or bicyclic, more preferably monocyclic five-membered ring heteroaromatics having from one to three nitrogen atoms and/or one oxygen or sulfur atom, mono-, bi- or tricyclic, preferably mono- or bicyclic, more preferably monocyclic six-membered ring heteroaromatics having from one to three nitrogen atoms as heteroatoms, especially pyridines such as 2-ethylpyridine, 3-ethylpyridine, 4-ethylpyridine and 5-ethyl-2-methylpyridine, preferably 2-ethylpyridine and 5-ethyl-2-methylpyridine.

Examples include the dehydrogenation of ethylbenzene to styrene, of cumene to α-methylstyrene, of butene to butadiene and of isopentene to isopentadiene (isoprene), in particular the dehydrogenation of ethylbenzene to styrene.

Suitable promoters for the inventive catalysts, in addition to cerium compounds, are advantageously compounds of calcium, magnesium, molybdenum, tungsten, chromium and titanium.

Suitable further promoters also include vanadium, copper, manganese, nickel, zinc, palladium, platinum, cobalt, aluminum, tin, silicon, lead, ruthenium, silver, gold, zirconium, rhodium, lanthanum, chromium, cadmium, barium or mixtures thereof.

The inventive hydrogenation catalyst advantageously has the following composition in relation to the sum of fresh and secondary feedstocks:
copper oxide corresponding to 0-80% by weight of CuO,
aluminum corresponding to 0-80% by weight of $Al_2O_3$ and
iron corresponding to 0-90% by weight of $Fe_2O_3$, and also
oxides selected from the group consisting of
potassium, cerium, magnesium, calcium, lanthanum, tungsten, molybdenum, titanium, tin, vanadium, manganese, nickel, zinc, palladium, platinum, cobalt, tin, silicon, lead, ruthenium, silver, gold, zirconium, rhodium, chromium, cadmium, barium, corresponding to 0-20% by weight
the components mentioned adding up to 100% by weight.

The inventive dehydrogenation catalyst more preferably has the following composition in relation to the sum of fresh and secondary feedstocks:
iron, corresponding to 40-90% by weight of $Fe_2O_3$,
potassium, corresponding to 1-40% by weight as $K_2O$,
cerium, corresponding to 1-25% by weight of $Ce_2O_4$, in particular 5-15% by weight of $Ce_2O_4$,
magnesium, corresponding to 0-10% by weight of MgO,
calcium, corresponding to 0-10% by weight of CaO,
tungsten, corresponding to 0-10% by weight of $WO_3$,
molybdenum, corresponding to 0-10% by weight of $MoO_3$,
vanadium, corresponding to 0-10% by weight of $V_2O_5$
the components mentioned adding up to 100% by weight.

The weight ratio of potassium (calculated as $K_2O$) to iron oxide (calculated as $Fe_2O_3$) is generally from 0.01:1 to 2:1, preferably from 0.1:1 to 1:1. The catalysts preferably additionally comprise further promoters (calculated as oxides) in a weight ratio relative to iron oxide of from 0.01:1 to 1:1, preferably of from 0.02:1 to 0.5:1.

Preference is given to not adding any doping elements to the secondary catalyst material.

The invention further relates to catalyst beds which consist to an extent of at least 25% by weight of inventive catalyst based on the total amount of catalyst of the corresponding catalyst bed. Advantageously, the catalyst beds consist of at least 30% by weight, preferably at least 50% by weight, of inventive catalysts. The inventive catalysts may be distributed uniformly over the catalyst bed mixed with catalysts from the prior art or be concentrated at one or more sites. In a catalyst system which consists of a plurality of reactors, i.e. a plurality of catalyst beds, one or more reactor(s), for example, is/are filled with the inventive catalysts, and the remaining reactors with the catalysts from the prior art. Preference is given to using exclusively inventive catalysts.

The invention further relates to the process for preparing the inventive catalyst, which comprises calcining secondary catalyst material of a spent (de)hydrogenation catalyst if appropriate and then grinding it and subsequently mixing, shaping and calcining it with fresh feedstocks of the corresponding (de)hydrogenation catalyst in a ratio of from 1:9 to 7:3.

Advantageously, the secondary catalyst material, before the grinding and the mixing with the fresh feedstocks, is subjected to a thermal treatment under oxygenous atmosphere at from 100 to 1500° C.

The secondary catalyst powder is mixed with the fresh feedstocks advantageously in a mixer, for example in a Mix-Müller.

The shaping and calcining are appropriately effected as described in the prior art (see, for example, DE-A 101 54 718).

To prepare the inventive catalysts, the feedstocks used, in addition to the secondary catalyst powder, may be compounds of the promoters as are present in the finished catalysts, or compounds which are converted during the preparation process to compounds as are present in the finished catalyst. It is also possible to add assistants to the feedstocks in order to improve the processibility, the mechanical strength or the pore structure. Examples of such substances are potato starch, cellulose, stearic acid, graphite and/or Portland cement. The feedstocks may be mixed directly in a mixer, kneader or preferably a Mix-Muller. Moreover, the feedstocks may also be slurried in a spray slurry and processed to a spray powder in a spray dryer. The feedstocks are preferably processed in a Mix-Muller or kneader with addition of water to give an extrudable mass. The extrudable mass is subsequently extruded, dried and calcined. Preferred catalyst shapes are strands, rings, tablets, annular tablets, extrudates or honeycombs. Particular preference is given to catalyst moldings or catalyst extrudates, having a diameter and a height of less than or equal to 10 mm. Preferred strand shapes comprise catalyst spheres having a diameter of less than 6 mm or catalyst honeycombs having a cell diameter of less than 5 mm or extrudates with diameter from 2 to 10 mm, in particular from 2.5 to 6 mm. The cross section of the extrudates may be round or in other shapes. Particular preference is given to extrudates with rotationally symmetric cross section, especially with a diameter of from 2 to 4 mm, preferably of 3 mm, and also to extrudates with a star-shaped cross section or those having a toothed-wheel cross section, especially with diameters of from 3 to 7, preferably 3.5 mm, 4.5 mm or 6 mm. Alternatively to an extrusion, the catalysts may also be shaped by tableting. The extruded or, if appropriate, tableted catalyst moldings are subsequently generally dried and subjected to a calcination. The drying is carried out preferably on a belt dryer at temperatures between 100° C. and 200° C. The calcination is carried out preferably in a rotary tube at temperatures between 500 and 1000° C., preferably between 700 and 1000° C., in particular between 800 and 950° C. and more preferably between 850 and 900° C. Especially in the course of calcination within the particularly preferred temperature range, carbonate-containing feedstocks are converted to oxides. In the particularly preferred temperature range, potassium oxide and iron oxide typically form mixed potassium ferrite crystal structures.

The invention will be illustrated in detail hereinbelow using the example of the process for dehydrogenating ethylbenzene to styrene.

The dehydrogenation of hydrocarbons can be carried out by all processes known to those skilled in the art. Preference is given to carrying out the dehydrogenation of alkylaromatics to alkenylaromatics in adiabatic or isothermal processes, especially in adiabatic processes. The reaction is generally distributed over a plurality of reactors connected in series, preferably radial flow reactors. Preference is given to connecting from two to four reactors in series. In each reactor is disposed a fixed bed comprising dehydrogenation catalysts.

In the dehydrogenation of ethylbenzene to styrene, as nowadays generally practiced in several stages, in so-called adiabatic processes, ethylbenzene is typically heated together with steam, advantageously in an amount of less than 30% by weight based on ethylbenzene, to temperatures around 500° C. by means of a heat exchanger and mixed with superheated steam from a steam superheater directly before entry into the first reactor, so that the desired inlet temperature in the first reactor is typically between 600 and 650° C. The mass ratio of steam (total steam) to ethylbenzene, on entry into the bed of the dehydrogenation catalyst in the first reactor, is advantageously from 0.7:1 to 2.5:1. Preference is given to working at a steam/ethylbenzene ratio of from 0.75:1 to 1.8:1, in particular from 0.8:1 to 1.5:1. The process is preferably operated at reduced pressure; typical reactor pressures are in the range from 300 to 1000 mbar. The liquid hourly space velocity (LHSV) based on the active volume of the beds (i.e. the volume of the beds minus any dead zones which are barely flowed through if at all) comprising dehydrogenation catalyst is generally from 0.2 to 0.7 l/h, preferably from 0.3 to 0.6 l/h and in particular from 0.32 to 0.58 l/h. The catalyst beds preferably arranged in a hollow cylindrical shape (radial flow reactors) are flowed through from the inside outward.

Before entry into the next reactor, the reaction mixture is advantageously brought again to temperatures of typically 600 and 650° C., advantageously using a heat exchanger by means of superheated steam. The pressure at the outlet of the last reactor should preferably not be more than 700 mbar, more preferably not more than 600 mbar and in particular not more than 500 mbar.

Alternatively, instead of the heat exchanger at the inlet of the second and any reactors which follow, it is also possible for a bed of an oxidation catalyst with oxygen supply for combustion of a portion of the hydrogen formed in the upstream reactor to be provided, as described, for example, in WO 2005/097715 and in WO 2006/018133.

The unsaturated compounds obtainable in the process according to the invention, for example alkenylaromatics or 1,3-alkadienes, may advantageously be polymerized to plastics or be used as starting materials for organic chemistry syntheses.

The inventive catalyst has distinctly lower preparation costs by virtue of the use of secondary catalyst material with a comparable activity and selectivity. Moreover, the costs for the disposal of the secondary catalyst material can be reduced.

EXAMPLES

Example 1

Process for Dehydrogenating Ethylbenzene

Example A

Inventive Catalyst

Secondary styrene catalyst strands were calcined at a temperature of 700° C. under an oxygenous atmosphere for 90 minutes. The thermally treated secondary catalyst strands were ground in order to obtain a particle distribution of from 1 to 700 μm. An elemental analysis was carried out.

Secondary catalyst powder and fresh feedstocks were mixed in a ratio of 40:60% by weight, so that the resulting catalyst had the following composition:
potassium, corresponding to 9.3% by weight as $K_2O$,
cerium, corresponding to 10.7% by weight of $Ce_2O_4$,
magnesium, corresponding to 2.1% by weight of MgO,
calcium, corresponding to 2.2% by weight of CaO,
molybdenum, corresponding to 2.4% by weight of $MoO_3$,
iron, corresponding to $Fe_2O_3$, difference from 100% by weight (arithmetic).

The catalyst powder was processed to catalyst strands in accordance with Example 8 of DE-A 101 54 718.

Example B

Inventive Catalyst

Catalyst strands were prepared from secondary catalyst material in accordance with Example 1, except that the secondary catalyst material was not subjected to any thermal treatment.

Example C

Comparative Example

Catalysts were prepared according to Example 8 of DE-A 101 54 718.

Dehydrogenation of ethylbenzene to styrene:
a) Dehydrogenation Under Isothermal Conditions In a one-stage isothermal test plant, 13.3 ml of the catalyst from Examples A to C were tested under the conditions specified in Table 1.

TABLE 1

Test conditions and results of the dehydrogenation of ethylbenzene to styrene under isothermal conditions

| Catalyst | Example A inventive | Example B inventive | Comparative Example C |
|---|---|---|---|
| Temperature | 620° C. | 620° C. | 620° C. |
| Pressure | 1 atm | 1 atmosphere | 1 atm |
| LHSV | 1.26/h | 1.26/h | 1.26/h |
| Steam/EB | 1.3 (kg/kg) | 1.3 (kg/kg) | 1.3 (kg/kg) |
| EB conversion | 73.5% | 72.9% | 73.7% |
| Styrene selectivity | 94.4% | 94.6% | 94.2% |
| Cutting hardness [N] | 48 | 47 | 50 | b) Dehydrogenation Under Adiabatic Conditions

In a two-stage adiabatic test plant, 434 ml in each case of the catalyst from examples A to C per reactor were tested under the conditions specified in Table 2.

TABLE 2

Experimental conditions and results of the dehydrogenation of ethylbenzene to styrene under adiabatic conditions

| Catalyst | Example A inventive | Comparative Example C |
|---|---|---|
| Temperature of reactor 1 | 617° C. | 616° C. |
| Temperature of reactor 1 | 620° C. | 621° C. |
| Pressure | 0.4 atm | 0.4 atm |
| LHSV | 0.48/h | 0.48/h |
| Steam/EB | 1.1 (kg/kg) | 1.1 (kg/kg) |
| EB conversion | 62.6% | 62.6% |
| Styrene selectivity | 97.4% | 97.3% |
| Cutting hardness [N] | 48 | 47 |

Example 2

Performance Assessment of Catalysts of Different Mixing Ratios Between Secondary and Fresh Catalyst Material In order to evaluate the performance of the individual catalysts, the following parameters were employed:

1. cutting hardness (CH)
2. deformability (D) by means of (mass of the shaped extrudates obtained)/(total mass used)
3. yield (Y)
4. economic viability (EV) by means of taking account of the particular material costs saved and the costs which arise through grinding and calcination of the secondary catalyst material and storage of this regenerated material
5. performance by means of multiplying factors 1 to 4/100

Table 3 lists said factors for the particular catalysts; FIG. 1 shows the performance determined as a function of the mixing ratio.

For the determination of the yield, the dehydrogenation of ethylbenzene to styrene was performed under isothermal conditions according to Example a.

TABLE 3

Performance data of different catalysts

| Mixing ratio | | | | | | |
|---|---|---|---|---|---|---|
| Fresh material | Secondary material | CH [N] | D | Y | EV | Performance |
| 0 | 100 | 0 | 0 | 0 | 0 | 0 |
| 25 | 75 | 29 | 0.3 | 0.4875 | 11.71 | 0.5 |
| 33 | 67 | 32 | 0.8 | 0.4965 | 13.82 | 1.76 |
| 50 | 50 | 35 | 1 | 0.4795 | 15.63 | 2.62 |
| 60 | 40 | 37 | 1 | 0.4774 | 15 | 2.65 |
| 90 | 10 | 39 | 1 | 0.4816 | 5.63 | 1.06 |
| 100 | 0 | 45 | 1 | 0.4883 | 0 | 0 |

What is claimed is:

1. A catalyst comprising: a ground, spent (de)hydrogenation catalyst material present in an amount of 10 to 70% by weight based on the catalyst, wherein the ground, spent (de)hydrogenation catalyst material comprising iron oxide; and a fresh catalyst material present in an amount of 30 to 90% by weight based on the catalyst, wherein the fresh catalyst material comprising iron oxide, wherein at least a portion of the iron oxide in the fresh catalyst material comprises a phase selected from the group consisting of hematite, potassium ferrite, and mixtures thereof.

2. The catalyst according to claim 1, wherein the spent catalyst material has been subjected to calcining at a temperature of 500 to 1000° C. prior to being ground.

3. The catalyst according to claim 1, wherein the spent catalyst material has been subjected to calcining at a temperature of 700 to 1000° C. prior to being ground.

4. The catalyst according to claim 1, wherein 15 to 85% by weight of the iron oxide in the spent catalyst material comprises $K_2Fe_xO_y$, based on the total iron oxide in the spent catalyst material, wherein x is a number of from 1 to 11 and y is a number of from 2 to 17, and a remainder of the iron oxide in the spent catalyst material comprises a phase selected from the group consisting of hematite, magnetite, and mixtures thereof.

5. The catalyst according to claim 1, wherein the ground, spent catalyst material is present in an amount of 25 to 65% by weight, and the fresh catalyst material is present in an amount of 35 to 75% by weight.

6. A process for preparing a catalyst according to claim 1, the process comprising:
    calcining a spent catalyst material comprising iron oxide; and
    subsequently mixing, shaping and calcining the spent catalyst material with a fresh catalyst material comprising iron oxide in a ratio of spent catalyst material:fresh catalyst material of 1:9 to 7:3;
    wherein at least a portion of the iron oxide in the fresh catalyst material comprises a phase selected from the group consisting of hematite, potassium ferrite, and mixtures thereof.

7. The process according to claim 6, wherein the spent catalyst material is ground prior to mixing with the fresh catalyst material.

8. The process according to claim 6, wherein the spent catalyst material is calcined under an oxygenous atmosphere at a temperature of 500 to 1000° C.

9. The process according to claim 6, wherein the spent catalyst material comprises no added dopant metals.

10. The process according to claim 6, wherein the spent catalyst material is mixed with the fresh catalyst material in a ratio of spent catalyst material:fresh catalyst material of 2.5: 7.5 to 6.5:3.5.

11. A catalyst bed comprising at least 25% by weight of a catalyst according to claim 1.

12. A process comprising: providing a hydrocarbon; and subjecting the hydrocarbon to conditions selected from dehydrogenating and hydrogenating conditions in the presence of a catalyst according to claim 1.

* * * * *